US010942158B2

(12) United States Patent
Basu

(10) Patent No.: US 10,942,158 B2
(45) Date of Patent: Mar. 9, 2021

(54) SYSTEMS AND METHODS FOR SELF PROVISIONING SENSOR BASED PROBES FOR PLANTS

(71) Applicant: Saswata Basu, Cupertino, CA (US)

(72) Inventor: Saswata Basu, Cupertino, CA (US)

(73) Assignee: 0Chain, LLC, Cupertino, CA (US)

( * ) Notice: Subject to any disclaimer, the term of this patent is extended or adjusted under 35 U.S.C. 154(b) by 275 days.

(21) Appl. No.: 15/923,826

(22) Filed: Mar. 16, 2018

(65) Prior Publication Data

US 2019/0128865 A1 May 2, 2019

Related U.S. Application Data

(60) Provisional application No. 62/489,843, filed on Apr. 25, 2017.

(51) Int. Cl.
*G01N 33/24* (2006.01)
*H04W 4/38* (2018.01)
(Continued)

(52) U.S. Cl.
CPC ........... *G01N 33/24* (2013.01); *G01N 33/246* (2013.01); *H04Q 9/00* (2013.01); *H04Q 9/02* (2013.01); *H04W 4/38* (2018.02); *A01C 21/007* (2013.01); *A01G 31/00* (2013.01); *G01N 2033/245* (2013.01); *H04L 67/12* (2013.01); *H04Q 2209/40* (2013.01); *H04Q 2209/883* (2013.01); *H04W 84/12* (2013.01)

(58) Field of Classification Search
CPC ................. G01N 33/24; G01N 33/246; G01N 2033/243; G01N 2033/245; A01C 21/007; A01G 31/00

USPC .............................................................. 73/73
See application file for complete search history.

(56) References Cited

U.S. PATENT DOCUMENTS 6,337,971 B1 * 1/2002 Abts .................... A01G 25/092
331/65
6,956,381 B2 10/2005 Dahan
(Continued)

OTHER PUBLICATIONS

Decagon Devices, Inc., EC-5 Soil Moisture Sensor User's Manual version 2, 2001-2012, https://dyacon.com/wp-content/uploads/2014/08/Decagon-Manual-EC-51.pdf.
(Continued)

*Primary Examiner* — Benjamin R Schmitt
(74) *Attorney, Agent, or Firm* — Levine's Tech Consulting, LLC; Frank E. Levine

(57) ABSTRACT

A sensing platform with at least one sensing device to sense underground and above ground environment parameters. A system of sensing environment parameters for a plant using a probe comprising: a first sensor board adapted to sense one or more environment parameters at one or more submerged depth located at flexible points of a location; a second sensor board adapted to done or more environment parameters at one or more surface points located at flexible points of the location; a circuit board adapted to communicate the sensed environment parameters to a central controller; adapted to operate in a low power mode. A system of sensing environment parameters for a field of plants using two or more probes using a fail-over central controller in a double star configuration and/or self learning algorithm.

20 Claims, 24 Drawing Sheets

(51) Int. Cl.
*H04Q 9/02* (2006.01)
*H04Q 9/00* (2006.01)
*H04W 84/12* (2009.01)
*A01G 31/00* (2018.01)
*A01C 21/00* (2006.01)
*H04L 29/08* (2006.01)

(56) References Cited

U.S. PATENT DOCUMENTS

| | | | |
|---|---|---|---|
| 2007/0208517 A1* | 9/2007 | Glenn | A01G 7/00 |
| | | | 702/19 |
| 2008/0129495 A1* | 6/2008 | Hitt | A01G 25/167 |
| | | | 340/539.26 |
| 2013/0341420 A1* | 12/2013 | Lister | A01G 25/167 |
| | | | 239/1 |
| 2015/0043519 A1* | 2/2015 | Hui | H04W 72/0453 |
| | | | 370/330 |
| 2015/0323491 A1* | 11/2015 | Miller | G01N 33/24 |
| | | | 205/789 |

OTHER PUBLICATIONS

Sentek Technologies, Drill & Drop Probe Installation Manual version 3, May 2015, https://www.fondriest.com/pdf/sentek_drill_drop_manual.pdf.

Bryan Lufkin, Gizmodo // Soil Sensors Can Cut Farmes' Water Use by a Quarter During a Drought, Jun. 22, 2015, https://www.cropx.com/gizmodo-swarms-of-soil-sensors-may-help-farmers-water-smarter-during-the-drought/.

* cited by examiner

SYSTEMS AND METHODS FOR SELF PROVISIONING SENSOR BASED PROBES FOR PLANTS

PRIORITY APPLICATIONS

For purposes of the USPTO extra-statutory requirements, the present application constitutes a utility application related to and claims the benefit of priority from U.S. Provisional Patent Application No. 62/489,843 filed on Apr. 25, 2017.

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

FIELD OF THE INVENTION

The present invention is in the technical field of agriculture. More particularly, the present invention is in the technical field of sensing plant environment parameters. More particularly, the present invention is in the technical field of underground sensing plant environment parameters.

BACKGROUND

Conventional sensor devices are typically short (e.g. Decagon probes) and do not have the depth to measure soil parameters. Other devices suffer from air gap problems (e.g. Sentek probes) and water stagnation problems (e.g. CropX probes). It is difficult to measure soil parameters several feet down because one needs to dig a large hole, then insert conventional sensor devices into the soil, and have a cable run up above the ground, which would need to be connected to a wireless telemetry device. Further, measuring soil parameters at multiple depths, one needs to install several of the sensor devices and run multiple cables above the ground. In the case of Sentek probes, air gap between the circular probe tube and the hole drilled is an issue as the probe tube may not have a tight fit with the soil environment. Additionally, there is a potential air gap between the metal plates and the inner lining of the probe tube. In the case of CropX probes, the sensor is located on the thread of the probe, where water can stagnate and lead to erroneous results of the state of the moisture in the soil environment.

SUMMARY OF THE INVENTION

The present invention is a sensing platform to measure the plant environment with a plurality of sensors at multiple depths in the soil as well as plurality of sensors above the soil at multiple heights.

A system and method of sensing environment parameters for a plant using a probe comprising: sensing using a first sensor board one or more environment parameters at one or more submerged depth located at flexible points of a location; sensing using a second sensor board one or more environment parameters at one or more surface points located at flexible points of the location; communicating using a circuit board the sensed environment parameters to a central controller; using a low power mode for operating.

A system and method of sensing environment parameters for a field of plants using two or more probes, each probe comprising: sensing using a first sensor board one or more environment parameters at one or more submerged depth located at flexible points of a location; sensing using a second sensor board one or more environment parameters at one or more surface points located at flexible points of the location; communicating using a circuit board the sensed environment parameters to a central controller; using a low power mode for operating with low frequency in a double star configuration.

DETAILED DESCRIPTION OF THE INVENTION

Figure 1A:
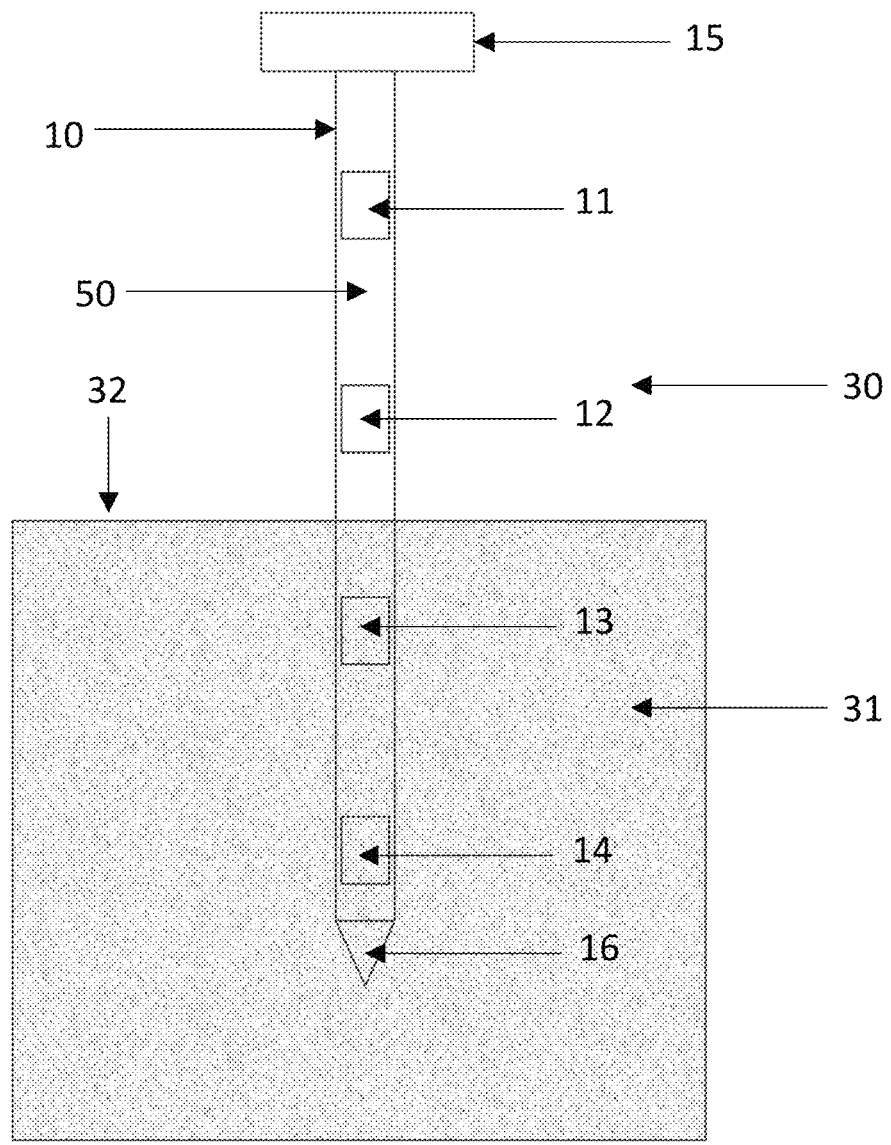
FIG. 1(a) is a front view of the probe, (b) is a side view of a manifestation of the probe, (c) is a front view of a manifestation of the probe; wherein the probe is one embodiment of the present invention.
Figure 1B:
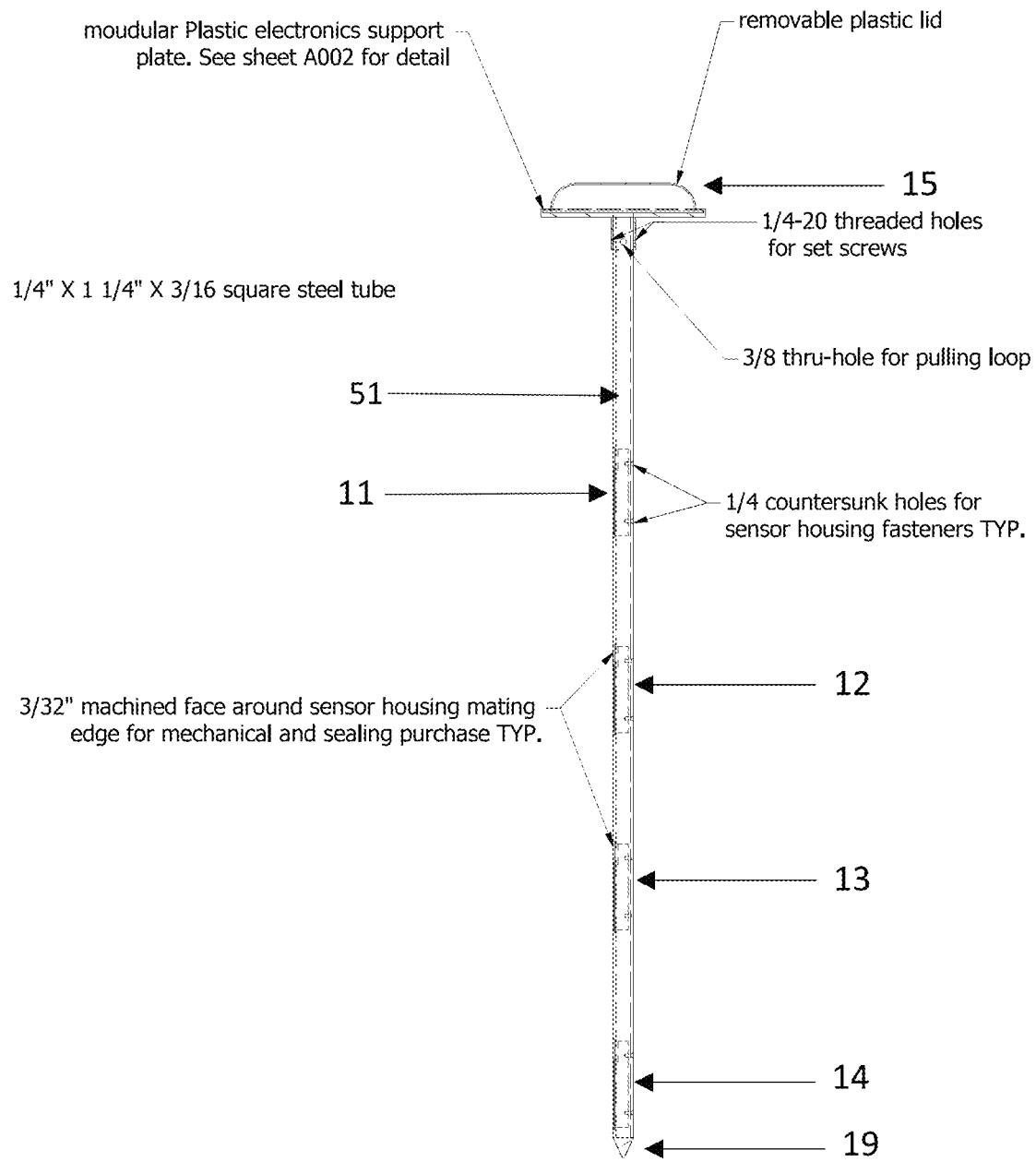
Figure 1C:
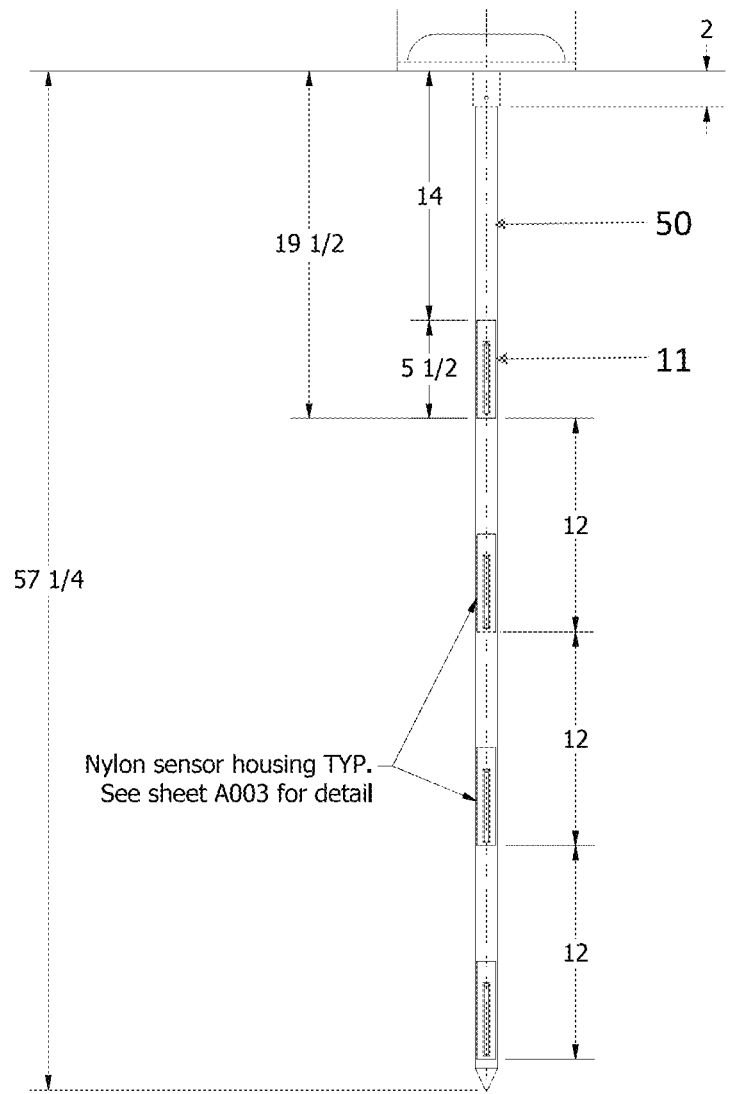

Referring now to the invention in more detail, in FIGS. 1(a)-(c) show a plant sensing platform 10 that has cut-outs or slots at different depths 11, 12, 13, 14, a top platform 15 to house a circuit board and a pointed end 16 to allow ease of installation. Each cut-outs or slots can house a sensor board 26 to sit in a housing 20 shown in detail in FIGS.

3(a)-(c), such that the sensor board 26 is flush with the platform face 50 and contacts the environment 30, 31. The environment 30, 31 could be different such as air 30 above ground surface 32 and soil 31 below ground surface 32. For hydroponic systems, the environment 32 is primarily aerated water. For aeroponic systems, the environment 32 is primarily air with sprayed water. The flush platform for the sensor allows moisture to drip down without stagnating, which would cause problems with measurements. The square pipe manifestation of the probe allows the window of the sensor housing to be in tight contact with the soil environment. The cut-outs or slots are located at points on the surface or submerged depths and can be adjusted to be at flexible points, i.e. the space coordinates of the housed sensor board with reference to a plant are not constant.

Figure 3A:
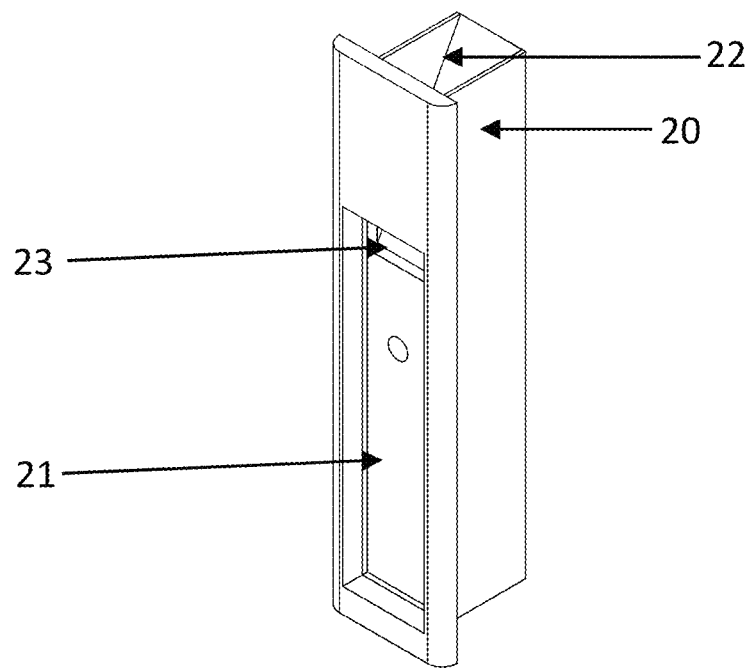
FIG. 3(a) is a perspective view of the sensor housing, (b) is a side view of the sensor housing, (c) is a perspective view of the manufacturing process of the sensor housing with the sensor board with epoxy and a glass or hydrophilic film.
Figure 3B:
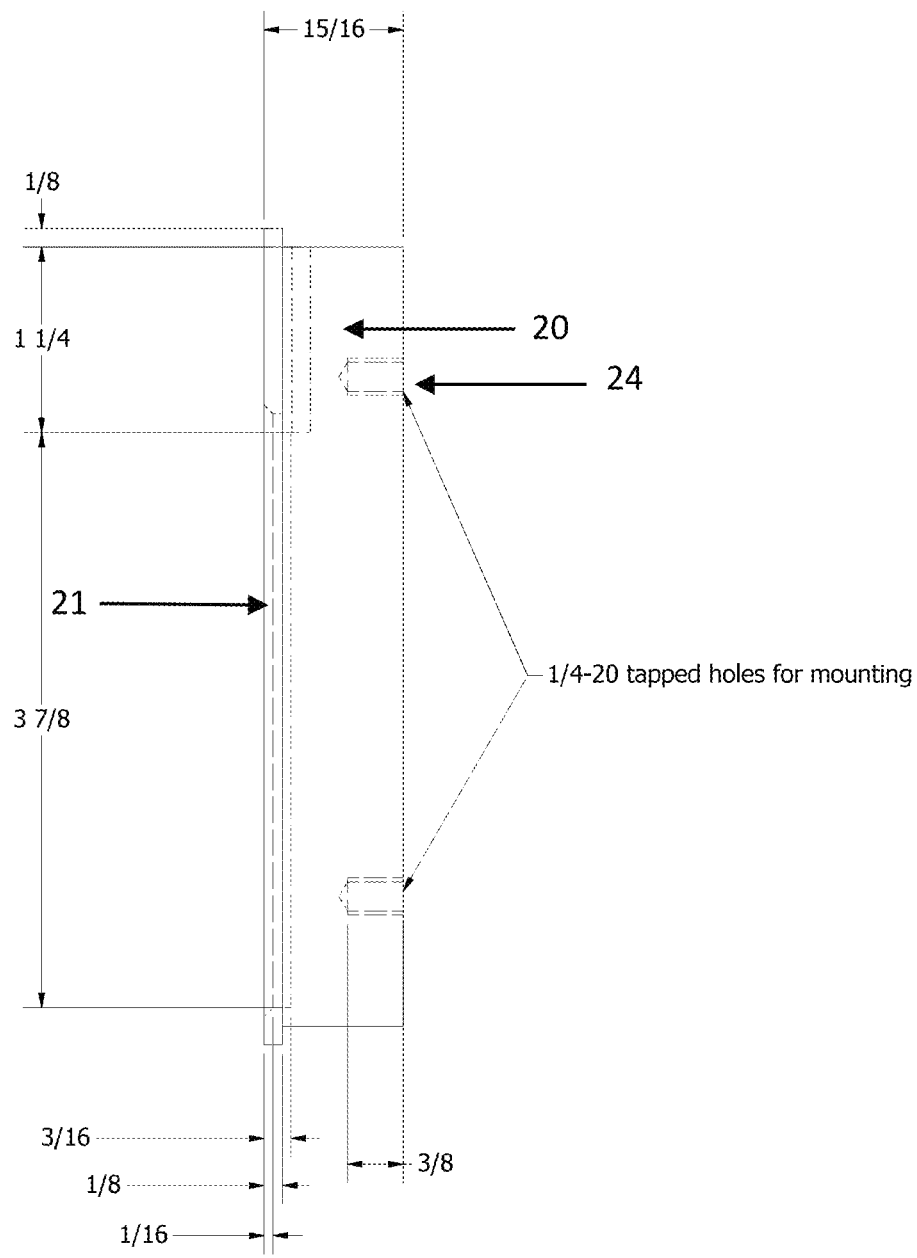
Figure 3C:
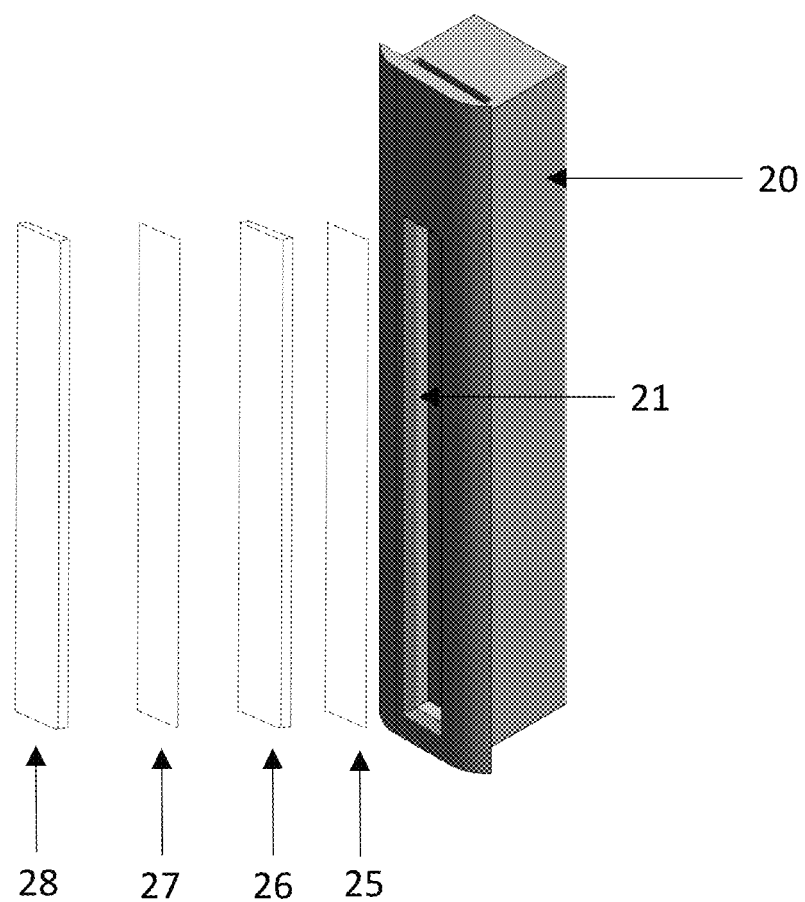

In more detail, referring to the invention of FIG. 3c, a thin layer of epoxy 25 is applied to have the sensor board 26 stick to the housing 20, and another layer of epoxy 27 or some other non-conductive coating would be applied on the face of the sensor board in the housing such that it forms a smooth water-resistant layer, and is flush with the platform surface 50, and when inserted into the ground, it will have a tight contact with the environment. Water will diffuse slowly into the epoxy layer until an equilibrium is reached which would prevent more water from coming in. With drying and wetting of the soil, there will be hysteresis effects as water molecules diffuse in and out of the epoxy layer coating, and over time the effects need to be calibrated out.

Still referring to FIG. 3c, a glass or a hydrophilic polyester film 28 is typically placed on the epoxy layer 27 to have a predictable distribution of water on the surface of the board and have additional water resistance. This will also help reduce or eliminate the hysteresis effects of water. Water will not diffuse into the glass or hydrophilic polyester film. Since there is very little or no diffusion, the advantage is that hysteresis effects over time would not take place and no additional calibration is needed. There may be minimal moisture ingress at the edges of the board through the epoxy layers, but this will not affect the measurement or have any residual hysteresis effects.

Figure 4A:
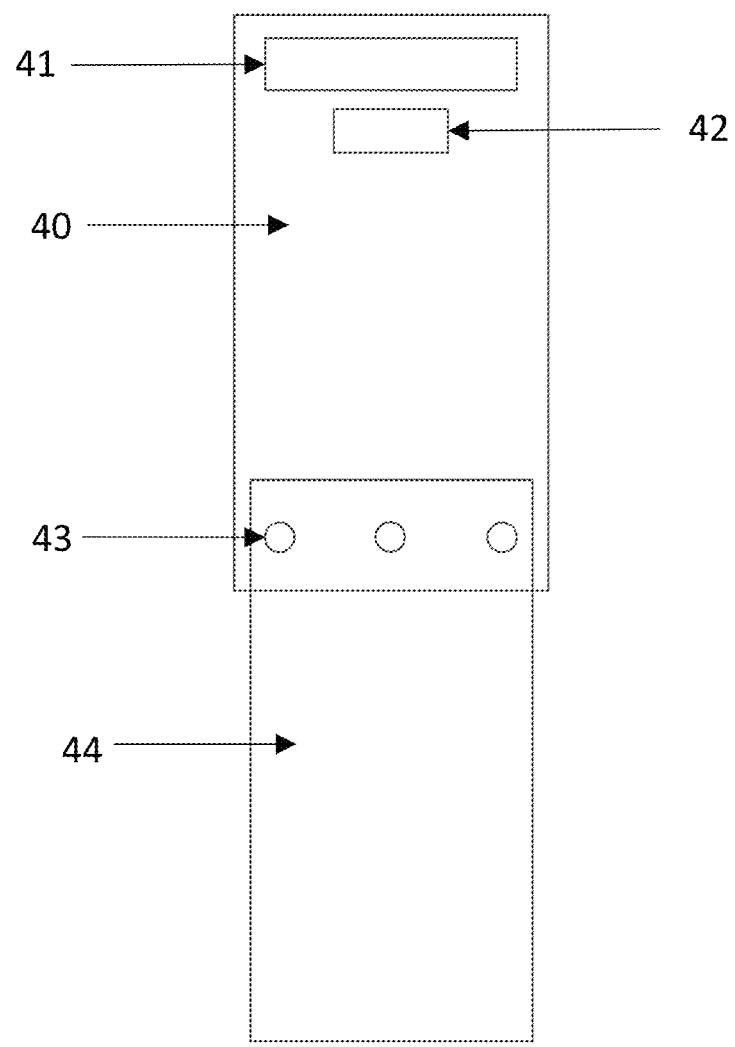
FIG. 4(a) is a top view of the component and sensor boards, (b) is a side view of the assembly of the sensor and component boards.
Figure 4B:
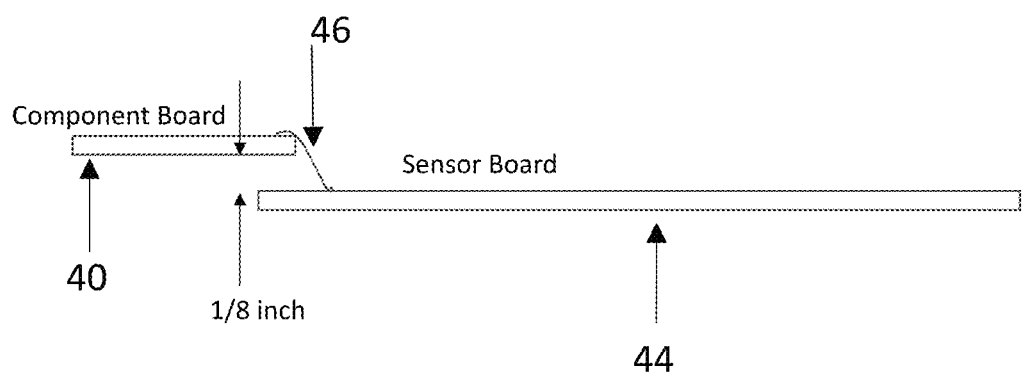

Referring now to the invention in more detail, in FIGS. 4(a)-(b), the sensor board 44 is typically a capacitive component made up of two or more conductive lines on the side facing the environment. One of the lines would be connected to the positive side of the circuit, while the other connected to the ground. To increase capacitance and keep the circuit simple, a 3-conductor co-planar design is utilized. The center conductor connected to the positive side of the circuit is meandered to increase the capacitance. The sensor board 44 is connected to a component board which has all the electronics that uses the variable capacitance of the sensor board 44 to measure the moisture and salinity of the environment. The vias 43 on the sensor board 44 connect the capacitive plates to the other side of the sensor board from which a solid wire 46 shown in FIG. 4(b) is connected to the component board 40. The sensor board 44 length is such that it is enough to make a good measurement at both lower and higher frequencies. At higher frequencies, transmission line effects reduce the effectiveness of the sensor board 44.

In one embodiment, the temperature sensor is typically placed on the component board 40 along with all other components. In another embodiment, the temperature sensor can be placed on the sensor board 44 to increase sensitivity to temperature variations of the environment. The sensor would then be mounted on the side that is not facing the environment to prevent any damage during installation.

Figure 6:
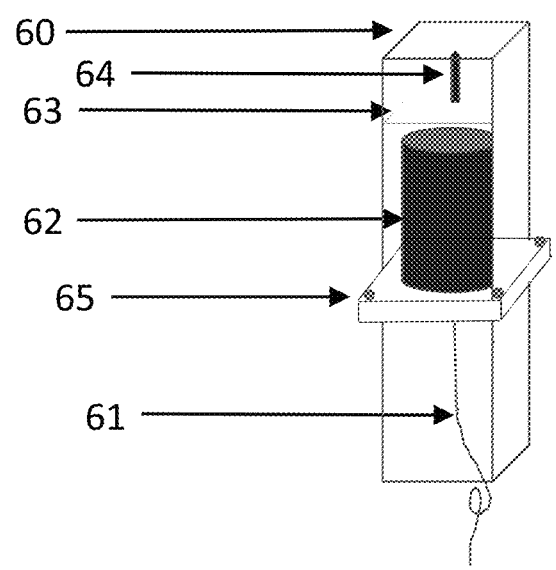
FIG. 6 is the perspective view of a manifestation of the probe top housing

In more detail, still referring to the invention of FIGS. 4(a)-(b), the two circuit boards, sensor board 44 and component board 40, are situated inside a plastic, glass, or metal housing as showing in FIGS. 3(a)-(c). The sensor board 44 sits inside a slot 21 on the housing 20, while the soldered component board is on the back side 22 of the housing 20. A cable 61 shown in FIG. 6 as a potential manifestation of the invention is typically run between the housings 20 by plugging into the headers 41 of the respective component boards 40 in the housing 20. The top end of the cable 61 comes out of the pipe 50 and attaches to the header 133 on the top circuit board 130 situated inside the probe top housing 60 as shown in FIG. 6 and FIG. 13. The electronics on the circuit board inside the probe top housing 60 typically consists of a microprocessor, A/D converter, and a RF circuit to enable the measurement, read the component 40 and sensor board 44 values, and then wirelessly transmit the measured data to the basestation 120 shown in FIG. 12. The term basestation also known as central controller used herein is broadly defined and is referring to a relay or central station that may collect and/or transmit information from one or more probes acting as a relay or center using radio frequency communication components. In one embodiment, the basestation is a center point that collects information from all the probes in the field of plants. In one embodiment, the basestation uses wi-fi, wireless LAN or local area network technology to collect the sensed environment parameters from the probes. In one embodiment, the basestation may relay the information to another basestation that eventually connects to a cellular or satellite network.

The basestation with one or more probes constitute a network that is connected using different wireless and wired networks available and known to a person of ordinary skill in the art to connect different computer devices including client and server systems. In an implementation, the network is publically accessible on the internet. In an implementation, the network is inside a secure corporate wide area network. In an implementation, network allows connectivity of different systems and devices using a computer-readable medium. In an implementation, the data including sensed environmental parameters have different privacy settings and a user interface that allows a user or administrator of the system to configure settings that allow data to be shared among select employees.

Figure 16:
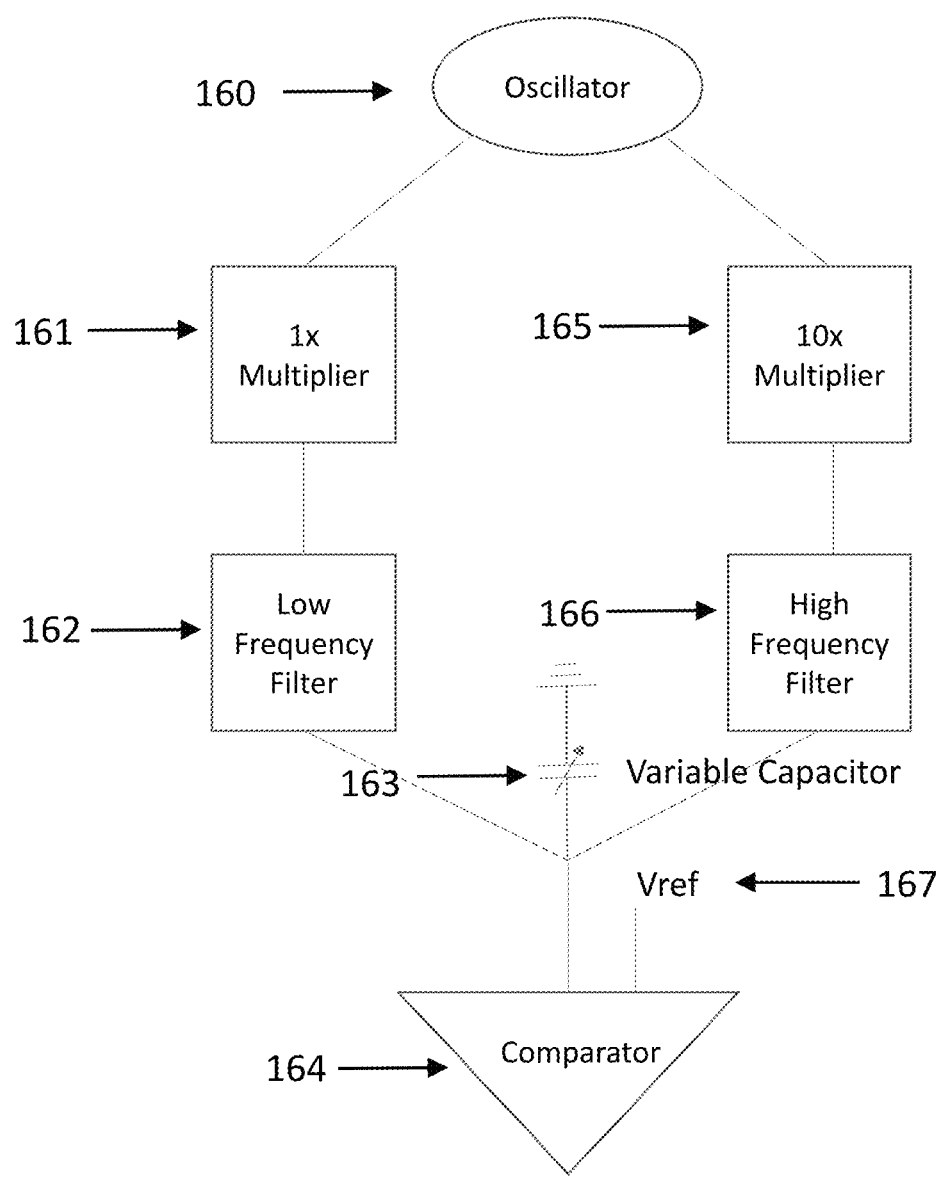
FIG. 16 is a block diagram view of the sensor circuit

The design details of the invention of the component board 40 is shown in FIG. 16. There are two frequency generators used to measure the moisture and salinity content separately. To lower cost of crystal oscillators and preserve space, one frequency generator 160 is used with a multiplier 161, 165 architecture. In addition, each frequency generator is filtered 162, 166 to prevent frequencies from ambience, such FM radio affecting the measurement. Moreover, a RF shield over the entire circuit is used to prevented unwanted RF picked up from the pipe or the sensor board feeding back to the component board circuitry. The generated signal from the frequency generator is then passed over a bridge circuit involving the sensor board 44 as the variable capacitor 163. The output of the capacitor voltage is then compared against a fixed reference voltage 167 at the input of the comparator 164, which is followed by gain stages to amplify the signal difference and then passed onto A/D converter to have a digital value sent to the probe top housing 60. An alternative would be to send the analog signal to the probe top housing 60 via the cable wires 61, and have the microprocessor which has an embedded A/D converter to process the signal.

Figure 2:
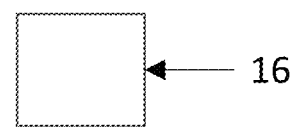
FIG. 2 shows top profile views of different manifestations of the probe platform.
Figure 2:
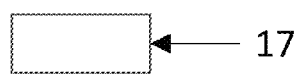
Figure 2:
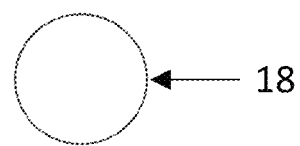

Referring to FIG. 2, the platform 10 can have a square 16, rectangular 17, or circular 18 cross-sectional profile in shape with different dimensions.

Referring to FIG. 1, the cut-outs such as 11, 12 on platform 10 can be on different faces such as 50, 51 at different depths. The cut-outs of the platform are such that the sensor housing 20 forms a flat rectangular base so that the mating of the two surfaces does not have leave any gap. On the back side of the cut-out are at least two threaded holes 24 for countersink screws to hold the sensor housing 20 together inside the platform 10.

The construction details of the invention as shown in FIG. 1 are that the platform 10 may be made of a hollow metal tube or different types of hard plastics such as Plexiglas, polycarbonate, fiberglass, steel and the like, or any other sufficiently rigid and strong material. Further, the various components of the housing 20 can be made of metal or different plastics such as nylon, ABS, and the like. Plastics would be a cheaper construction of the invention and the sensor board 44 would measure the soil parameters more accurately since it will not have to account for any electromagnetic effects typically associated with a metal pipe. The pointed end 16 of the probe shown in FIG. 1 allows the probe to be installed with ease by simple hammering in.

The housing 20 has a slot 21 for the sensor 44 and component 40 board to sit inside in a snug manner so that the face of the sensor board 44 is flush with the window of the housing 20. The window of the housing is about 1" inch wide and 4" in height to average the soil parameter measurement over the length of the sensor. The housing 20 is such that it can accommodate two circuit boards, sensor board 44 and the component board 40. The sensor board 44 sits flush with the housing window 21 and overlaps the component board 40 which has the components facing away from the window. The housing height increases from say 2-3 mm which is slightly larger than the height of the sensor board to 10 mm at the overlap and then up to 15 mm at the opening 23. The opening 23 of the housing is such that the circuit boards, once assembled together, can be slid through and be set inside the window portion. Epoxy is poured through the opening 22 to seal the boards from any water ingress and a layer of epoxy 27 would be placed on top of the sensor board 44 to prevent water ingress through the soil. Alternatively, a glass or polyester film 28 would be placed on the sensor board to prevent any long-term measurement effects of salt and water on the sensor board 44.

The sensor board 44 sits a little back from the edge, say about $\frac{1}{16}$", to prevent damage from soil abrasion when the pipe 10 is hammered down into the ground with all the sensor boards 44 inside the housing 20. The sensor board 44 could be manufactured using a flexible PCB so that it can wrap around the pipe or have different types of design to average the measurement vertically and horizontally. For example, in one embodiment, it is inexpensive to make the sensor board out of a standard PCB.

The sensor board 44 is made separate from the component board 40 for couple of reasons. One is to slow down any ingress of water to reach the electronic components easily. The other is to have the sensor board 44 sit closer to the soil, without having the backside of the component board 40 in contact with the soil. While there is a layer of epoxy 27 separating the soil and the PCB, the layer is very thin of $\frac{1}{16}$" and the first point of moisture breach will be at the window 21, and with the component board 40 separated by a plastic housing, it is unlikely to get damaged at the first ingress. Unless the moisture travels all the way to the contact point of the sensor 44 and component 40 boards, there will be no effect on the measurement.

The component board 40 has DIP switches and cable connectors that stick out of the board and away from the housing opening 22. This makes the assembly of the probe easier for multiple sensors and lowers its cost. Each of the probe's sensor need to be addressed separately for measurement and calibrated separately. The assembler can attach the board to a cable connector and have a DIP switch to select the board depth level without the need to do any hardware design changes to the component board.

Referring now to FIG. 1, the pipe may be extended vertically above ground where we can have additional sensors. The sensor 44 and component 40 boards could be of different circuitry from the underground sensors and detect different parameters such as humidity, light intensity, and volatile gases.

Figure 7:
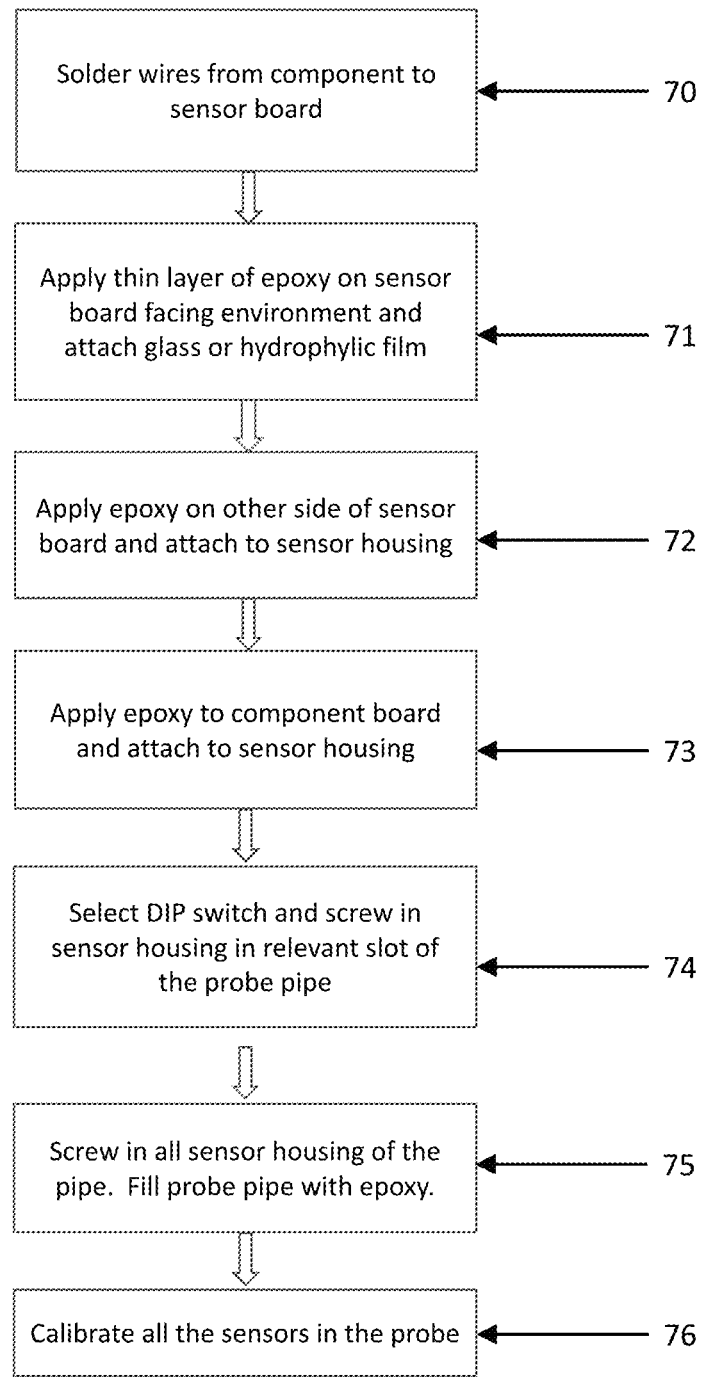
FIG. 7 is the assembly process of the probe platform with sensor housing and circuit boards

The assembly of the probe is as shown in FIG. 7. The first step 70 is to have the three wires soldered from the component board to the sensor board. The second step 71 is to apply a thin layer of epoxy on the sensor board that faces the environment and attach a thin glass or hydrophilic film on top of the board. The third step 72 is to apply epoxy on the surface of the slot on the sensor housing and around all its edges, and then have the sensor board bond on to the surface and edges. The fourth step 73 is to apply epoxy on the sensor housing and push the component board down to bond it with the housing. The fifth step 74 is to select the DIP switch, plug the cable 61 which is pre-inserted into the probe platform, and insert the housing 20 into the relevant cut-outs 11, 12, 13, 14 of the probe platform 10. After all the housings 20 are inserted into the probe platform 10, the probe platform 10 is filled with epoxy 75 close to the top of the probe platform. The last step then is to conduct calibration 76 for each of the sensors in the probe platform 10 by dipping the probe in multiple mediums with different moisture and salinity levels.

The probe platform 10 as shown in FIG. 1 has a welded tip 16 at the bottom for ease of insertion into a drilled hole.

Figure 5A:
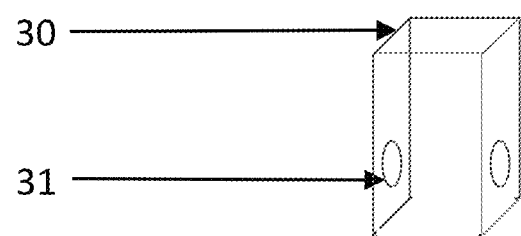
FIG. 5(a) is the perspective view of the lifting cap, (b) is the perspective view of the driving cap.

The probe platform 10 also has a driving cap shown in FIG. 5a, which fits on top of the probe and is used for hammering the probe inside a pre-drilled smaller hole.

Figure 5B:
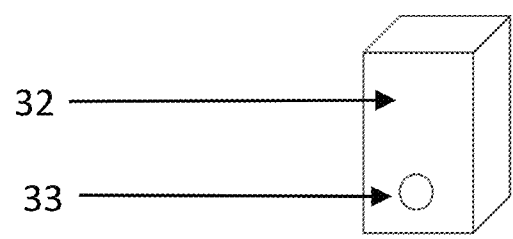

The probe platform also has a U-shaped lifting cap, shown in FIG. 5b, which fits on top of the probe and can be used with an off the shelf Hi-Lift Jack to be able to lift the probe up from the environment it is embedded in.

The probe top housing shown in FIG. 6 displays a different manifestation from FIG. 1, where all of electronics fit on top of the probe, has a cable 61 that runs from the sensor housing. A battery 62 is placed inside the probe top housing 60 to power the electronics.

Figure 8:
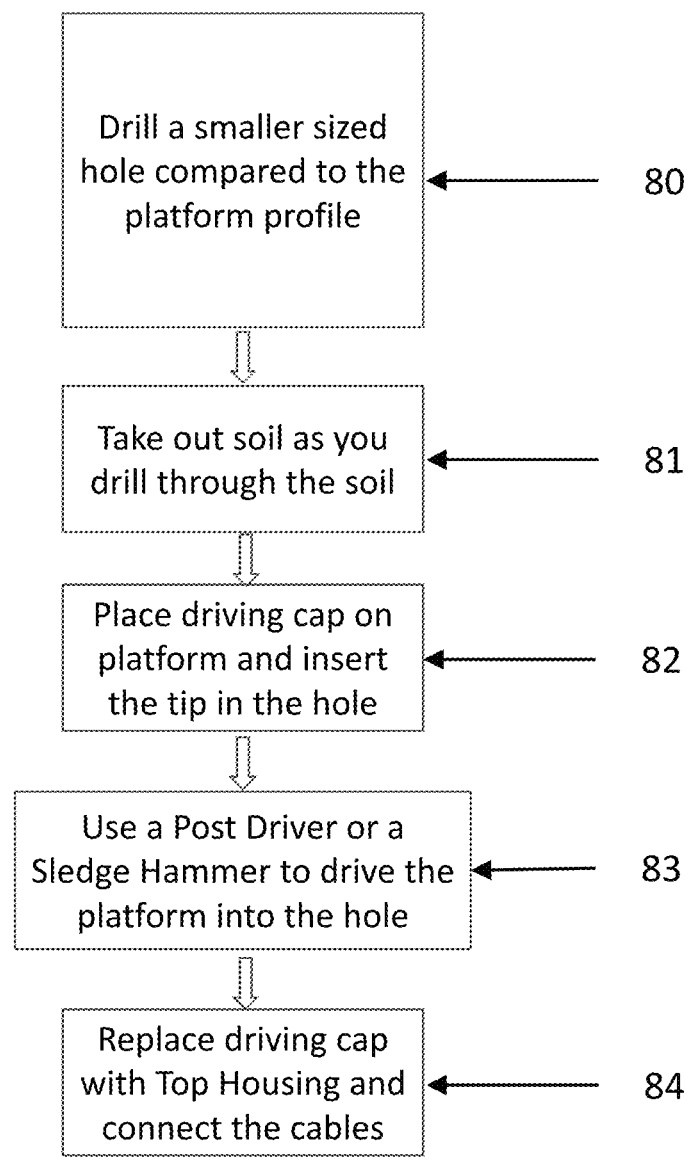
FIG. 8 is the installation process of the probe platform.

The process of installing a probe as in FIG. 8 is to drill a hole slightly smaller 80 than the inner dimensions of the tube and then hammer the probe in to get a tight fit so that the sensor board has a good contact with the environment and there are no air gaps which would cause a discrepancy in accurate measurement of the moisture and saline content of the environment. Additionally, because of the flush and smooth surface of the sensor window, as water is added on top of the soil, it drains uniformly on the sensor, providing a more accurate representation of the soil environment.

Figure 9:
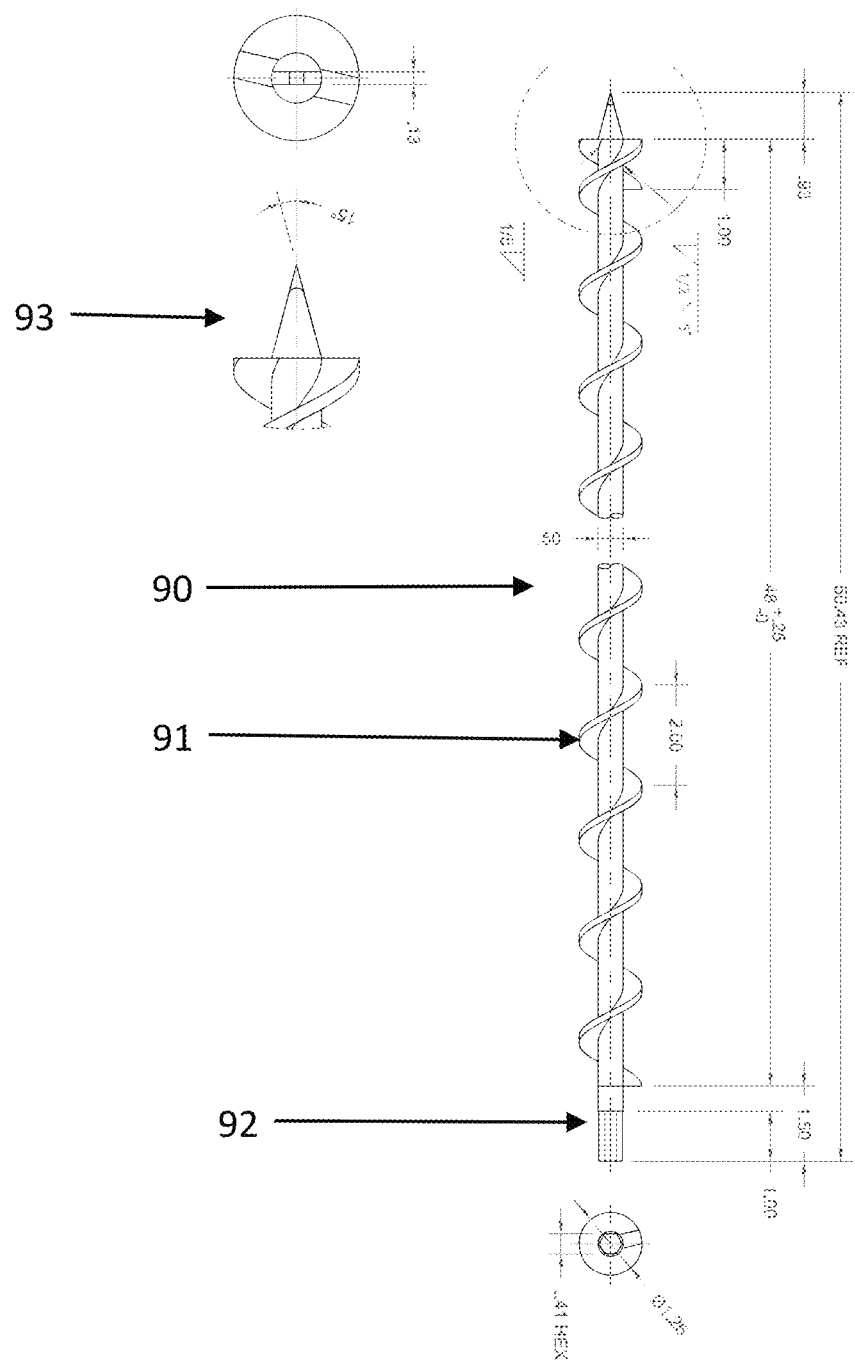
FIG. 9 is the design of the drill bit used in the installation.

The drill bit 90 is designed as shown in FIG. 9 with a thick neck 92 to prevent breakage as it drills through different layers of soil. The tip 93 is made of carbide or a hard material to break through any rocks as it drills down. The top soil layer is sandy and as it drills deeper, it is more clay type.

The flute 91 of the drill needs to be at least the length of the pipe that is inserted in the hole. Typically, during drilling, the drill tool is inserted one foot and moved up to remove any soil clinging to the drill, and then reinserted to drill another foot, and so on. The process of drilling and removing soil on the drill every foot ensures a clean drill hole, and avoids the drill getting stuck in the hole.

A square pipe 16 as shown in FIG. 2 is better for insertion in a smaller circular hole as it pushes the soil at the edges of the pipe, and have minimal compaction at the sensor window 21, which would otherwise distort measurements of the soil parameters, at least initially.

The design of the probe platform 10 allows for the shock and vibrations from the hammering to go right through the outer body of the probe and has very little impact on the component board 40. The soldered wires 46 connecting the boards and epoxy layers are elastic by nature and are stretched a little but can endure small vibrations.

Figure 10:
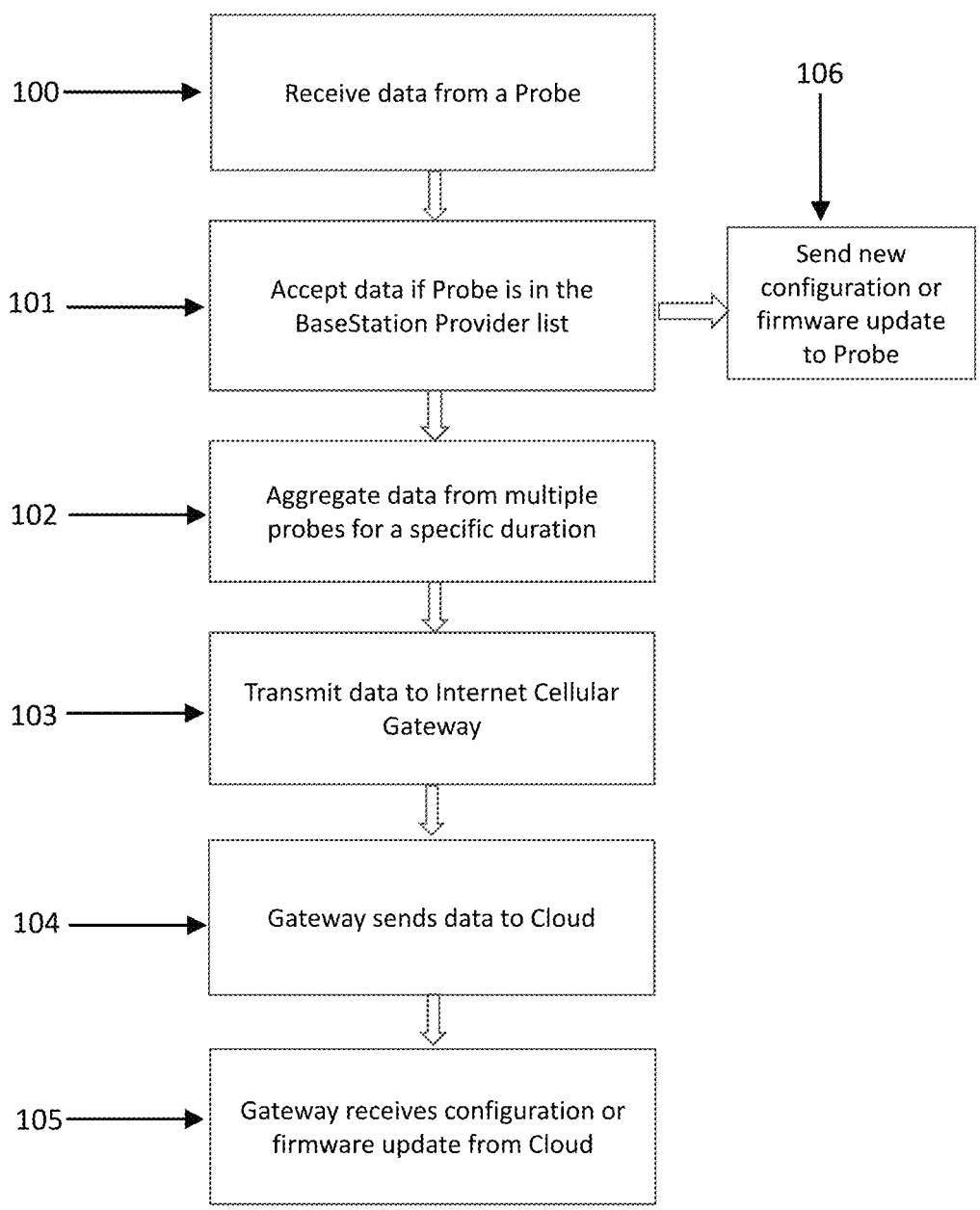
FIG. 10 is a view of the design of the basestation firmware.
Figure 11:
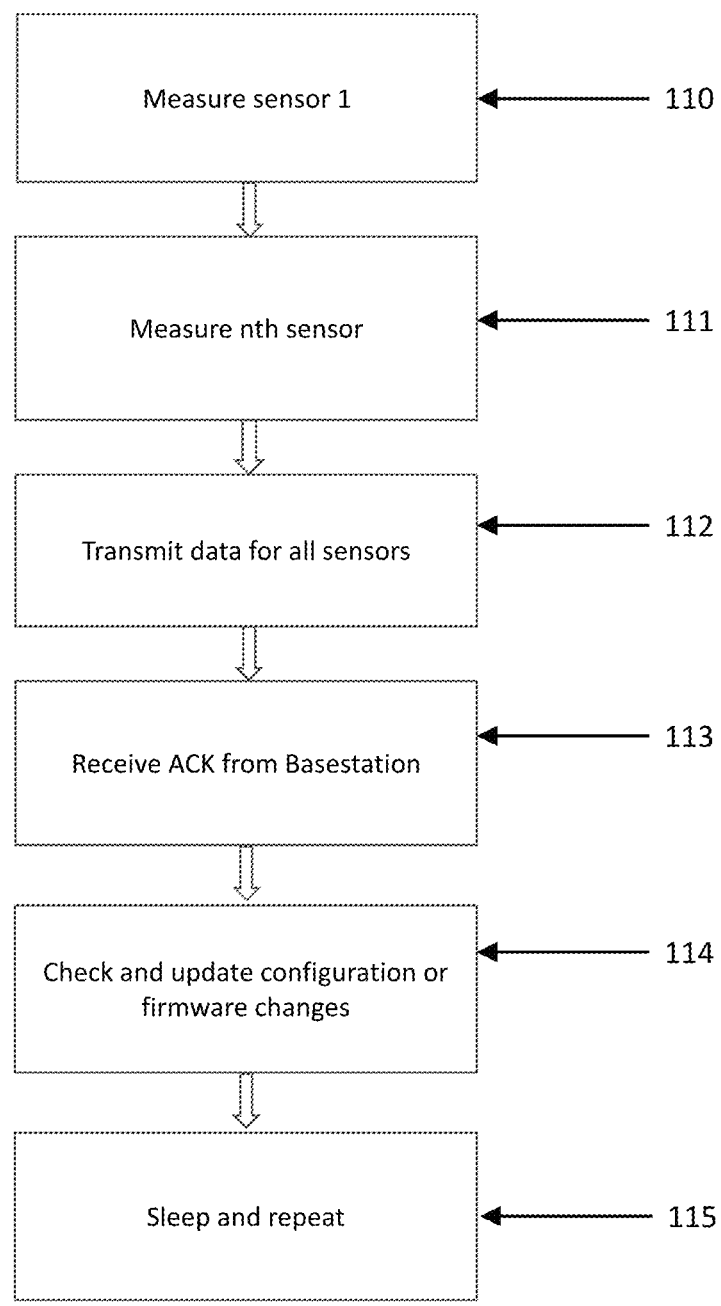
FIG. 11 is a view of the design of the probe platform firmware.
Figure 15:
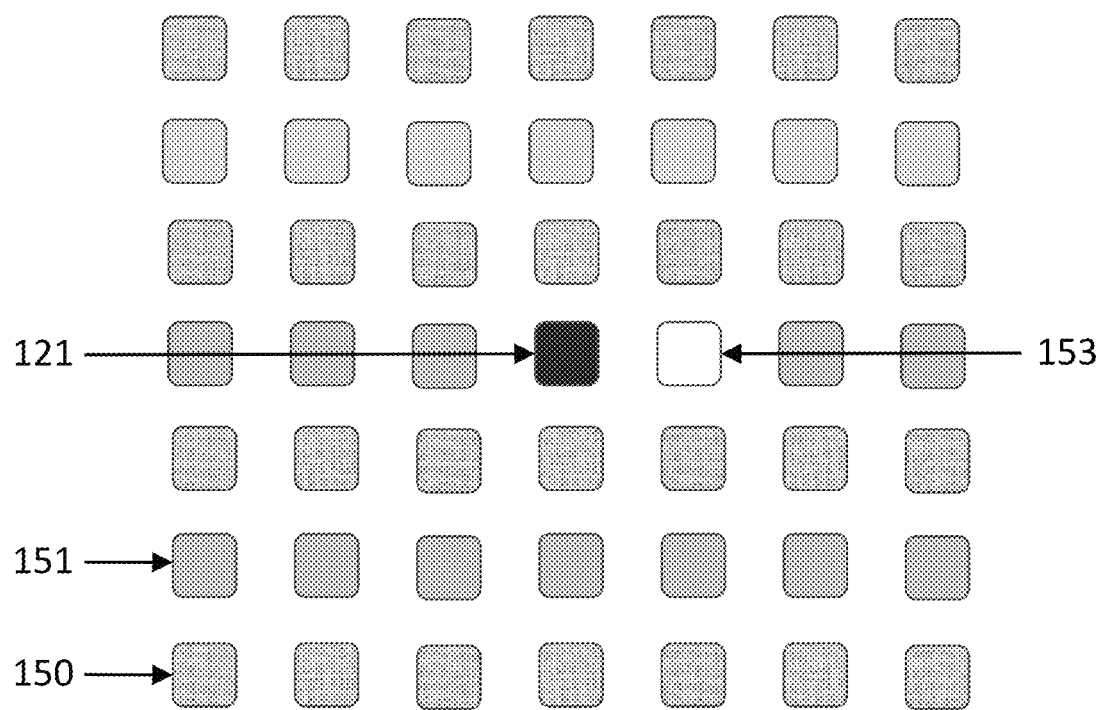
FIG. 15 is a view of an architecture of a redundant basestation system

The firmware design of the probe 130 measurement and communication to the basestation 120 is as shown in FIG. 11. The probe sleeps 115 for some duration of time, say sixty (60) seconds and then wakes up to take readings 110, 111 from multiple sensors. The readings take an average of about one (1) second after which the data is transmitted out. A nearby basestation 120, allowed to accept communication from this probe, would then pick up the transmission and respond with an acknowledgement as depicted in FIG. 10. To have redundancy and scalability at a low cost, an additional basestation 153 can be situated nearby as a 1+1 configuration as shown in FIG. 15 where both basestations 120, 153 are set up to transmit data from different sets of probes 150 and 151 to the cloud. If one basestation fails, the other takes over communication of the probes that had been talking to the failed basestation. The fail-over mechanism is that the probe will talk to a different basestation if the current basestation fails as long as it is close to it. The basestation has a list of probes it listens to. When one basestation fails, the other basestations add the disconnected probes to their list. This happens centrally at the cloud and the list is updated at the basestation. The cloud sends appropriate configuration changes to the basestation during the failover. A cloud used herein is in the cloud computing context that is the delivery of computing services—servers, storage, databases, networking, software, analytics, and more—over the Internet ("the cloud"). Data or information collected over the probes in a field of plants can be collected and accessed in the cloud.

The cloud can send addition configuration information and can also do an over-the-air firmware upgrade for its basestation or probe. For instance, it can increase the probe time delay between measurements to accommodate more probes per basestation, and a list of probes to accept messages from as they are added to the network or upon basestation failure. The timing information of the measurement at the probe is communicated during the "ACK" part of the message to all the probes. Other configurable items are the frequency of operation between the probe and the basestation.

Figure 14:
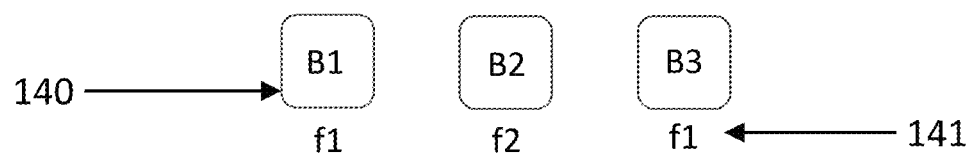
FIG. 14 is a view of the frequency planning for the basestations in a large scale deployment

The two basestations in the 1+1 configuration has the same frequency of operation 140 with the probes. The neighboring basestations operate in a different frequency band 141 to prevent interference among the nearby basestations as shown in FIG. 14. A low power mode for the probes can be achieved by the 2-star (double-star or 1+1 configuration) topology, because the basestation operates in lower frequency and requires less power to connect to the probe compared to a single-star topology. For example, low power mode is in the range of 10 dBm to 0 dBm for the probes and low frequency ranges for ISM band is 400 MHz to 900 MHz.

Figure 12:
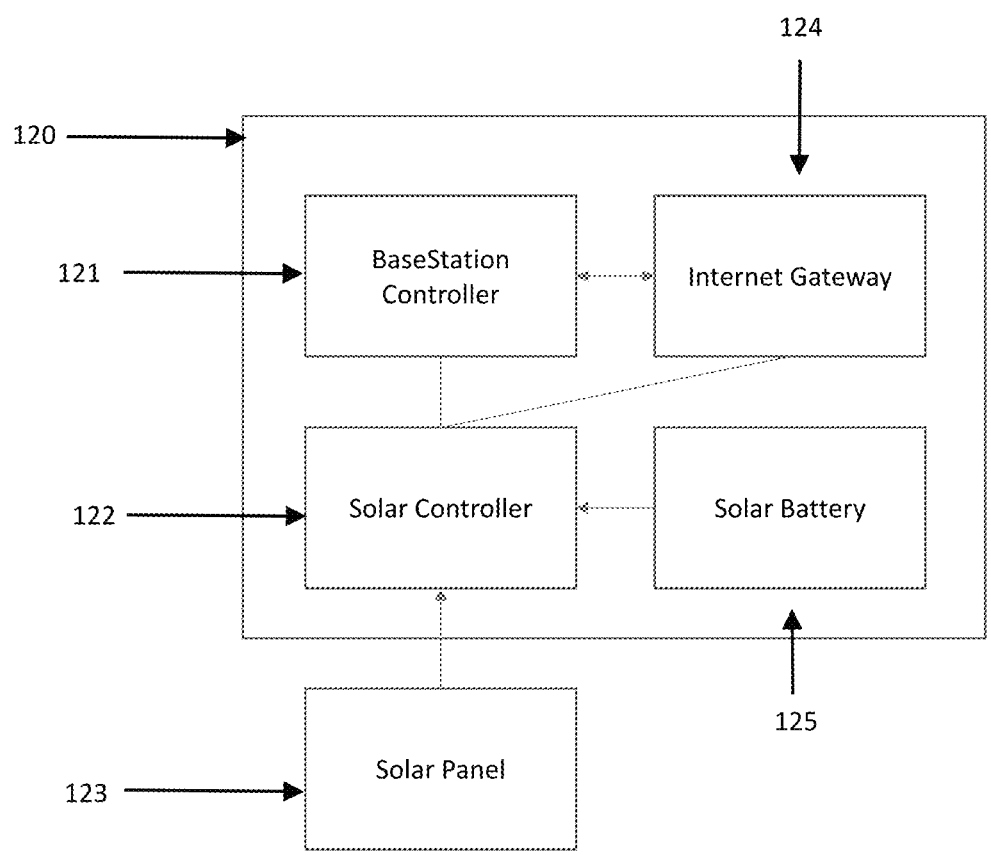
FIG. 12 is a view of the basestation hardware system
Figure 13:
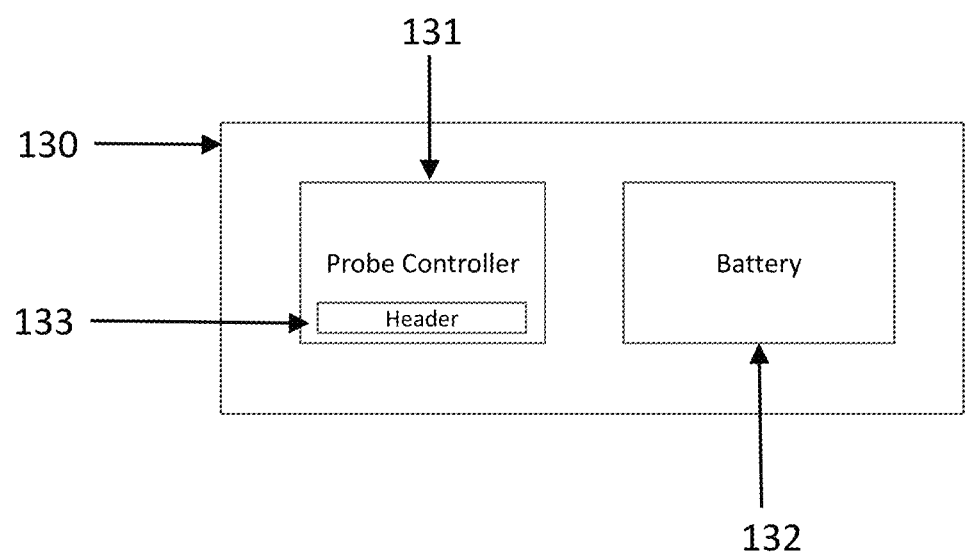
FIG. 13 is a view of the probe top housing hardware system

The basestation 120 consists of components depicted in FIG. 12. The basestation controller 121 is the same as the probe controller 131 but the firmware code is different. The basestation controller 121 communicates with a cellular gateway 124 designed to connect to the cellular network. Both the basestation controller 121 and the internet router 124 are housed inside a solar cabinet panel. The solar power system consists of a solar panel 123, rechargeable battery 125, and a solar controller 122 which provides enough DC power to last a week without sunlight.

The basestation 120 assembles all the data from all the probes, stores them in memory for a specific duration, and then transmits it to the cloud. The duration is configurable from the cloud.

Figure 17:
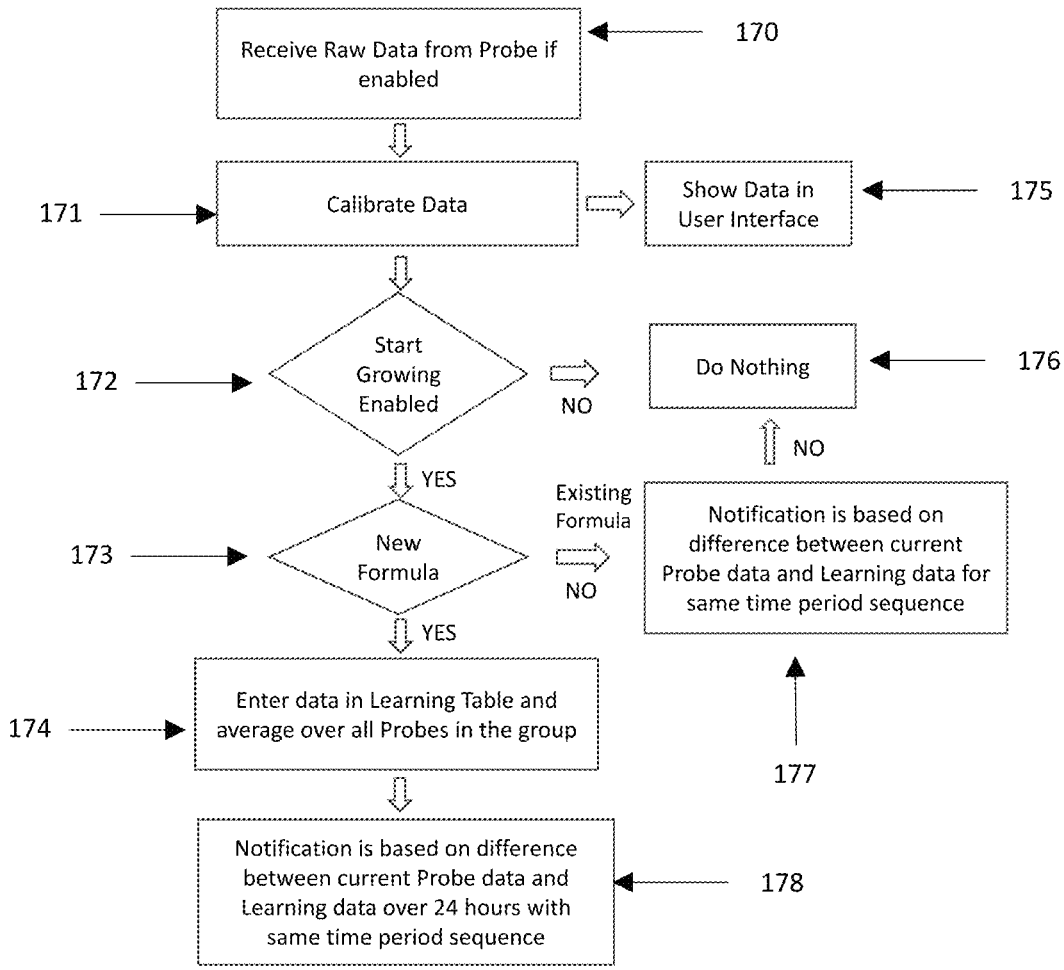
FIG. 17 is a view of the cloud architecture to process received data and generate notifications

The cloud receives data from multiple probes as shown in FIG. 17 and accepts them if the probe is enabled 170. It then calibrates the data 171 based on calibration parameters of each sensor. After calibration is completed, the data is checked for notification 177, 178 based on a stored formula 173. If the incoming data exceeds the min and max of the stored formula data point in consecutive instances over a period of duration, then notifications are displayed.

Several components described here, including clients, servers, and engines, can be compatible with or implemented using a cloud-based computing system. As used here, a cloud-based computing system is a system that provides computing resources, software, and/or information to client systems by maintaining centralized services and resources that the client systems can access over a communications interface communications interface, such as a network. The cloud-based computing system can involve a subscription for services or use a utility pricing model. Users can access the protocols of the cloud-based computing system through a web browser or other container application located on their client system.

Figure 18:
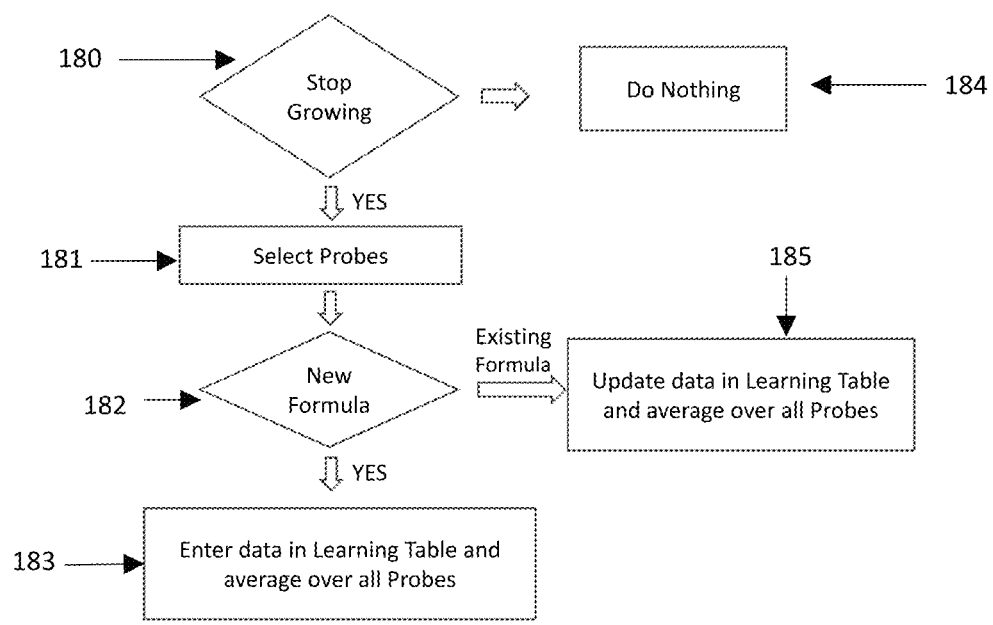
FIG. 18 is a view of the self-learning algorithm

The self-learning algorithm to create a self learning formula for the probe platform is shown in FIG. 18. The learning start and stops with the user clicking on the "Start Growing" button 180. When the user clicks on the 'Start Growing' button 180, the user either selects 'Create New Formula' or 'Use Existing Formula'. Each Formula has a Formula ID. The Formula collection has consecutive hour data entries in a sequence irrespective of the when the data is timestamped. The timing sequence is based on the relative time of when the user clicked on the 'Start Growing' button. When the user clicks on the Stop Growing button, user can Create a New Formula or Override an Existing Formula 182. The user selects the probes 181 that would be used to create the formula. The hour data for all the probes are then averaged and the min and max points for that hour over all the probes are entered for the formula. Each formula data point has a user selected deviation percentage that is applied for notification purposes.

Self learning algorithms may include one or more components of artificial intelligence known to a person of ordinary skill. For example, depending on the desired input parameters for the plant environment, the self learning algorithm may use one or more of the search based, perceptrons, clustering, decision trees, rules-based or machine learning algorithms. Real-time active feedback provided by a large number of sensors can be automated to be monitored and configured using statistical artificial intelligence.

When the user clicks on the "Start Growing" button 172, the user selects an "Existing Formula" or creates a "New Formula" 173. If a "New Formula" is created, then it is updated on the fly with data from the incoming probes 174. In one or more embodiments, the Existing Formula or New Formula, herein referred to as the learnt formula is selected based on feedback from the data collected from the existing probes using self learning algorithm. Any notification will be based on the last 24 hour averaged data entries from all the probes 178, unless the data exceeds the absolute max and min values.

User can enter observation for a group of probes or an individual probe at any point of time. This observation serve as machine learning training sets, and is used to predict future events and propose pre-emptive actions to the user.

The advantages of the present invention include, without limitation, an easy and cost-effective way to install underground and above ground sensors to measure environment parameters without air gap or moisture stagnation problems because of its flush design, and without long term moisture effects on the measurement, and can endure shock and vibration during installation.

In broad embodiment, the invention is a sensor platform to measure environmental parameters.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

A detailed description of one or more implementations of the invention is provided here along with accompanying figures that illustrate the principles of the invention. The invention is described in connection with such implementations, but the invention is not limited to any implementation. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The structures and modules in the figures may be shown as distinct and communicating with only a few specific structures and not others. The structures may be merged with each other, may perform overlapping functions, and may communicate with other structures not shown to be connected in the figures.

The invention claimed is:

1. A method of sensing environment parameters for a plant using a probe comprising:
    sensing, using a first sensor board, one or more environment parameters at one or more submerged depth located at flexible points of a location;
    sensing, using a second sensor board, one or more environment parameters at one or more surface points located at flexible points of the location;
    communicating using a circuit board the sensed environment parameters to a central controller;
    using a low power mode for operating as per the frequency of a basestation in a double star configuration.

2. The method of claim 1 further comprising:
    installing the probe at the location by hammering the probe in.

3. The method of claim 1, wherein the location is part of a hydroponic or aeroponic system.

4. The method of claim 1 further comprising:
    minimizing the hysteresis effect of water by placing a glass or a hydrophilic polyester film on top of an epoxy layer covering the sensor boards;
    separating the sensor boards from a component measuring the sensor data to get closer for the sensor boards with the environment and protect the component from damage.

5. The method of claim 1, wherein the low power mode uses a battery or a solar panel.

6. A method of claim 1, wherein the one or more environment parameters include one or more of the following: moisture, salinity, or temperature.

7. The method of claim 1, wherein the circuit board uses a radio frequency components to communicate wirelessly to a local area network and the central controller is located within the wireless range irrespective of availability of any cellular or satellite wireless network coverage.

8. A method of sensing environment parameters for a field of plants using two or more probes, each probe comprising:
    sensing, using a first sensor board, one or more environment parameters at one or more submerged depth located at flexible points of a location;
    sensing, using a second sensor board, one or more environment parameters at one or more surface points located at flexible points of the location;
    communicating using a circuit board the sensed environment parameters to a central controller;
    using a low power mode for operating as per the frequency of a basestation in a double star configuration.

9. The method of claim 8 further comprising: recovering the sensed environment parameters using another central controller as fail-over when the central controller fails.

10. The method of claim 8, wherein one or more probes are selected for learning a new formula and the learnt formula is subsequently applied to the remaining probes.

11. A system of sensing environment parameters for a plant using a probe comprising:
    a first sensor board adapted to sense one or more environment parameters at one or more submerged depth located at flexible points of a location;
    a second sensor board adapted to sense one or more environment parameters at one or more surface points located at flexible points of the location;
    a circuit board adapted to communicate the sensed environment parameters to a central controller;
    wherein the system is adapted to operate in a low power mode as per the frequency of a basestation in a double star configuration.

12. The system of claim 11 further comprising:
    the probe made of rigid and strong material including one or more of steel, plexiglass, polycarbonate or fiberglass to allow hammering the probe in at a desired location.

13. The system of claim 11, wherein the location is part of a hydroponic or aeroponic system.

14. The system of claim 11 further comprising:
    a glass or a hydrophilic polyester film covering placed on the top of an epoxy layer covering the sensor boards to minimize the hysteresis effect of water;

separated sensor boards from a component measuring the sensor data to get closer contact for the sensor boards with the environment and protect the component from damage.

15. The system of claim 11, wherein the low power mode uses a battery or a solar panel.

16. A system of claim 11, wherein the one or more environment parameters include one or more of the following: moisture, salinity, or temperature.

17. The system of claim 11, wherein the circuit board uses a radio frequency components to communicate wirelessly to a local area network and the central controller is located within the wireless range irrespective of availability of any cellular or satellite wireless network coverage.

18. A system of sensing environment parameters for a field of plants using two or more probes, each probe comprising:

a first sensor board adapted to sense one or more environment parameters at one or more submerged depth located at flexible points of a location;

a second sensor board adapted to sense one or more environment parameters at one or more surface points located at flexible points of the location;

a circuit board adapted to communicate the sensed environment parameters to a central controller;

wherein the system is adapted to operate in a low power mode as per the frequency of a basestation in a double star configuration.

19. The system of claim 18 further comprising: another central controller adapted to recover the sensed environment parameters for fail-over when the central controller fails.

20. The system of claim 18, wherein one or more probes are selected for a self learning a new formula and the learnt formula is subsequently applied to the remaining probes.

* * * * *